United States Patent [19]
D'Angelo et al.

[11] Patent Number: 5,989,840
[45] Date of Patent: Nov. 23, 1999

[54] ESTIMATION OF ACTIVE INFECTION BY HELIOBACTER PYLORI

[75] Inventors: Joseph P. D'Angelo; Jin Zhe, both of Miami, Fla.

[73] Assignee: Americare International Diagnostics, Inc., Miami, Fla.

[21] Appl. No.: 08/865,089

[22] Filed: May 29, 1997

[51] Int. Cl.[6] ............................................. G01N 33/554
[52] U.S. Cl. .................... 435/7.32; 422/101; 422/56; 422/50; 436/113; 436/518; 435/12; 435/6
[58] Field of Search ................... 435/7.32, 12, 6; 422/56, 50, 101; 548/126; 436/113, 165; 128/771; 204/403

[56] References Cited

U.S. PATENT DOCUMENTS

| | | | |
|---|---|---|---|
| 4,066,403 | 1/1978 | Bruschi | 23/230 B |
| 4,194,063 | 3/1980 | Frank et al. | 435/12 |
| 4,297,173 | 10/1981 | Hikuma et al. | 204/1 T |
| 4,350,660 | 9/1982 | Robinson et al. | 422/90 |
| 4,426,451 | 1/1994 | Columbus | 436/518 |
| 4,548,906 | 10/1985 | Sekikawa et al. | 436/113 |
| 4,568,518 | 2/1986 | Wolfbeis et al. | 422/56 |
| 4,713,165 | 12/1987 | Conover et al. | 204/403 |
| 4,719,085 | 1/1988 | Jacobs | 422/56 |
| 4,748,113 | 5/1988 | Marshall | 435/12 |
| 4,769,216 | 9/1988 | Chandler et al. | 422/58 |
| 4,769,467 | 9/1988 | Imai | 548/126 |
| 5,008,078 | 4/1991 | Yaginuma et al. | 422/56 |
| 5,091,080 | 2/1992 | Van Eikeren et al. | 210/188 |
| 5,116,759 | 5/1992 | Klainer et al. | 435/288 |
| 5,198,335 | 3/1993 | Sekikawa et al. | 435/4 |
| 5,238,613 | 8/1993 | Anderson | 264/22 |
| 5,252,292 | 10/1993 | Hirata et al. | 422/98 |
| 5,286,624 | 2/1994 | Terashima et al. | 435/12 |
| 5,344,546 | 9/1994 | Kiesele et al. | 204/415 |
| 5,393,496 | 2/1995 | Seymour | 422/101 |

(List continued on next page.)

OTHER PUBLICATIONS

"Determination on Ammonia in Saliva Using Indophenol, an Ammonium ELectrode and an Enzymatic Method: A Comparative Investigation", Huizenga et al., J. Clin. Chem. Clin. Biochem., vol. 20, 1982, pp. 571–574.

Vijaykumari, S. et al, Cytobios, vol. 82 (331), pp. 251–260, (abstract), 1998.

Patel, P. et al, Gastroenterol., vol. 106 (4), part 2, p. A156 col. 1, Abstract 2, 1994.

Jung, H. et al, The Soul journal of Medicine, vol. 31, No. 4, pp. 231–246, 1990.

Luzza, F et al, FEMS Immunology and Med. Microbiol., vol. 10 (3–4), pp. 285–288, 1995.

Hopkins, R.J. et al, Am. J. Med., vol. 97, Sep., pp. 265–277, 1994.

Karnes, W.E. et al, Gastroenterol, 1991, vol. 101, pp. 167–174, 1991.

Mertz, H. et al, Digestive Diseases and Sci., vol. 36, No. 1, Jan. pp. 1–4, 1991.

Bertocchi, P et al, Brosensors and Bioelectronics, vol. 11 (No. ½), pp. 1–10, 1996.

Dunn, B.E. et al, Infect. Immun., Jun. 1989, vol. 57 (61, pp. 1825–1833.

De Stoppelaar, J.D., J. Dent. Res, vo. 61 (Spec. issue) 1982, p. 225.

(List continued on next page.)

Primary Examiner—James C. Housel
Assistant Examiner—Ginny Allen Portner
Attorney, Agent, or Firm—Herbert L. Lerner; Laurence A. Greenberg

[57] ABSTRACT

Disclosed is a diagnostic apparatus for estimating an active *Heliobacter pylori* infectious agent in saliva, comprising in combination an immunoassay chamber in which a first portion of said saliva is subjected to serological test for antibody to said infectious agent and a chemical reaction chamber in which a second portion of said saliva is subjected to chemical analysis for an ammonia constituent thereof.

17 Claims, 3 Drawing Sheets

U.S. PATENT DOCUMENTS

| | | | |
|---|---|---|---|
| 5,411,893 | 5/1995 | Eden et al. | 436/165 |
| 5,420,014 | 5/1995 | Cripps | 435/7.32 |
| 5,420,016 | 6/1995 | Boguslaski et al. | 435/12 |
| 5,439,801 | 8/1995 | Jackson | 435/12 |
| 5,443,080 | 8/1995 | D'Angelo et al. | 128/771 |
| 5,462,064 | 10/1995 | D'Angelo et al. | 128/771 |
| 5,492,841 | 2/1996 | Craig | 436/534 |
| 5,494,640 | 2/1996 | Simon et al. | 422/2.05 |
| 5,506,148 | 4/1996 | Munkholm | 436/111 |
| 5,507,289 | 4/1996 | Essen-Moller | 128/635 |
| 5,552,276 | 9/1996 | Mochida et al. | 435/6 |
| 5,554,339 | 9/1996 | Cozzette et al. | 422/50 |
| 5,565,328 | 10/1996 | Bascomb et al. | 435/25 |
| 5,620,900 | 4/1997 | Tanzer | 436/113 |
| 5,709,837 | 1/1998 | Mori et al. | 422/56 |
| 5,719,052 | 2/1998 | Ito et al. | 435/287.1 |

OTHER PUBLICATIONS

Hurzenga, J.R et al, J. Clin. Chem. Clin. Biochem., 1982, vol. 20, pp. 571–574.

Killeen, G. F. et al, Analytical Biochem, vol. 215, 1993, pp. 284–291.

Matsuura, M. et al, 1990, Microbiol Immunol., vol. 34, #5, pp. 467–470.

Meyerowitz, C. et al, 1992, J. Dent. Res., vol. 71, (spec. issue), p. 521.

Singer, D.L. et al, Arch. orol. Biology, vol. 28(10), 1983, pp. 923–930.

Shuto, R. et al, Nippon Rinsho Dec., 1993, vol. 51(12) pp. 3132–3137, see summary (English Abstract).

Weinholt et al, 1993, vol. 694, Annals of the N.Y. Academy of Science, pp. 340–342.

Wolfbeis, O.S. et al, 1986 Analytica Chemica Acta, pp. 321–327, vol. 185.

Yamada, T. et al, J. Clin. Invest., vol. 52(6), 1973, p. 91.

Kobayashi, R. et al, 1992, vol. 40(5), Chem. Pharm. Bull., pp. 1327–1328.

ESTIMATION OF ACTIVE INFECTION BY *HELIOBACTER PYLORI*

BACKGROUND OF THE INVENTION

1. Field of the Invention

The invention relates generally to methods and devices used for determination of analytes in saliva or other body fluid, and in particular, pertains to an integrated device and method to carry out chemical and immunochemical analysis simultaneously and including a sensor strip for determination of ammonia.

2. Description of the Related Art

*Helicobacter pylori* (formerly called *Campylobacter pylori*) was first isolated by Warnell and Shall in 1983 (Marshall B. J., Warren J. R., Lancet 1984:1:1311–5). *H. pylori* is the most widespread bacteria infection with an estimated worldwide prevalence of 50% (Marshall B. J., Epidemiology of *H. pylori* in Western countries. In: Hunt R. H., Tytgat G. N. J., eds. *Helicobacter pylori:* Basic Mechanisms to Clinical Cure. Dordrecht: Kluwer Academic Publishers. 1994:75–84; Hazell S. L., *H. pylori* in developing countries. In: Hunt R. H. Tytgat G. N. J., eds. *Helicobacter pylori:* Basic Mechanisms to Clinical Cure, Dordrecht: Kluwer Academic Publishers, 1994:85–94). *H. pylori* is a very important pathogen in several diseases of the stomach and duodenum. *H. pylori* is associated with type B gastritis, duodenal ulcer, gastric ulcer, and gastric cancer.

A variety of methods has been developed for diagnosis of *H. pylori* infection and evaluation of eradication of *H. pylori* following antibacterial treatment.

U.S. Pat. No. 5,498,528 teaches a method for detection of *H. pylori* strain comprising the steps of contacting a saliva sample suspected of containing *H. pylori* directly with a urea containing medium selective for growth of *H. pylori* and having a pH of about 5.5 to 7.5, and incubating the sample for a time sufficient for detection of *H. pylori* growth in at least 80% of true positive samples. The method is based on hydrolysis of urea contained in the growth medium by urease enzyme produced by *H. pylori* and detection of a hydrolysis product by release of a radioactive label from urease or by a color change resulting from action on a pH indicator. The time required to obtain a result by the method disclosed is a function of temperature, approximately 2–3 days when incubated at 23–25° C. and 4–6 hours when incubated at 35–37° C.

U.S. Pat. No. 5,479,935 teaches an ambulatory system for recording and analyzing gastroesophageal reflux. The system comprises a digital recorder, an analysis software package and a catheter for measurement of changes in esophageal impedance. Gastroesophageal reflux can be detected with a pH above 4. The invention allows for recording and analysis of reflux on a non-invasive basis, by using pairs of externally worn impedance sensors. Other bio-parameters, such as pH or pressure can be measured simultaneously with impedance measurement.

U.S. Pat. No. 5,477,854 teaches a system and a method for monitoring intragastrointestinal concentrations of ammonium during prolonged periods, as an indicator of the presence and activity of an intragastrointestinal *H. pylori* infection. The system may be used in the evaluation of treatments for *H. pylori* infection in the patient.

U.S. Pat. No. 5,439,801 teaches an improved test for the detection of the presence of urease associated with *H. pylori* in a biopsy specimen. The hydrolysis of urea by urease is detected by a combination of at least two dye indicators showing a color change. Most positive results occur in 2–10 minutes and all occur in no more than four hours.

U.S. Pat. No. 5,438,985 teaches a method and a system for ambulatory recording of the pH and the presence of various materials in compartments of the gastro-intestinal tract. The invention also reports the pH pattern in relation to the prevalence of the materials, and analysis to which degree such materials are in active or inactive states in their normal or foreign compartments. This is useful in situations, for example, when duodenal material is refluxed into the stomach and esophagus. The invention involves a gastrointestinal catheter with a pH sensor and a combined light absorption and fluorescence sensor, a signal recorder and processor, and a written report producer.

U.S. Pat. No. 5,420,016 and U.S. Pat. No. 5,314,804 teach a rapid method for determining the presence of *H. pylori* in a biological tissue specimen by detecting the presence of urease in the tissue. The system employs a multilayer test device for the detection of ammonia generated from urea at the presence of urease in the specimen.

U.S. Pat. No. 5,420,014 teaches a method of detecting contemporary infection by *H. pylori* in a mammal. The method is based on the formation of complex between a specific IgG antibody in said mucous secretion and an antigen component from *H. pylori*. The antigen component is immobilized onto a solid support.

U.S. Pat. No. 5,262,156 teaches an assay for detecting *H. pylori*. The assay involves an ELISA for urine samples, and includes a kit wherein the antigenic composition is immobilized on a solid support.

U.S. Pat. No. 4,947,861 teaches a non-invasive method for detection of *C. pylori*. A breath sample is collected from a patient ten minutes after the patient ingests a quantity of urea. The sample is dehydrated by passing through a solid-state body of alkaline hygrosopic material and analyzed for ammonia. The presence of ammonia indicates presence of *C. pylori* in the stomach.

U.S. Pat. No. 4,882,271 teaches a method for the serological detection of *C. pylori*. An antigen for the detection of *C. pylori* infections is purified from *C. pylori*. The antigen can be used in a variety of assays including radioimmunoassay, ELISA, latex agglutination, complement fixation, and indirect hemagglutination.

The urea breath test based on the extremely high endogenous urea activity of *H. pylori* is a reliable and non-invasive method with high sensitivity and specificity suitable for diagnosis and evaluation tests; however, the application of the urea breath test is restricted by high cost in isotope-labeled material, time, expensive equipment, and undesirable radioactive exposure to $C^{14}$.

Against this background there remains a need for a method of diagnosing *C. pylori* that is rapid, non-invasive, and able to distinguish infection in an active state from dormant or non-living residues.

SUMMARY OF THE INVENTION

In accordance with this invention, it has been found that a novel non-invasive method for diagnosis of active *Heliobacter pylori* infection is based on simultaneous detection of antibody to the *H. pylori* and abnormal level of an ammonia constituent in a body fluid such as blood or saliva. Since antibody to the *H. pylori* lasts for a long period of time even with eradication of *H. pylori,* a serological test alone cannot predicate whether the bacteria infection is active. Ammonia concentration in a body fluid is affected by many diseases, and hence ammonia estimation alone cannot pinpoint exact cause of abnormal ammonia value. Combining the information obtained for ammonia analysis and the serological test, however, affords a novel test for active *H. pylori* requiring only small samples of body fluid and minimal inconvenience to the patient.

Also in accordance with this invention, a diagnostic apparatus for estimating an active Heliobacter pylori infectious agent in saliva comprises in combination an immunoassay chamber in which a first portion of said saliva is subjected to serological test for antibody to said infectious agent and a chemical reaction chamber in which a second portion of said saliva is subjected to chemical analysis for an ammonia constituent thereof. The presence of antibody to the *H. pylori* as shown by serological test coupled with abnormal level of ammonia indicates active *H. pylori* infection, while a positive serological result with normal ammonia constituent level indicates an *H. pylori* infection that is inactive or limited. Moreover, in accordance with this invention, quantitative or semi-quantitative analysis of ammonia and antibody levels in saliva can be used to monitor the eradication of *H. pylori*.

A method in accordance with this invention of estimating an active *H. pylori* biological infectious agent in a body fluid such as blood or saliva, comprises in combination subjecting a first portion of said fluid to serological test for antibody to said *H. pylori* infectious agent and subjecting a second portion of said fluid to chemical analysis for an ammonia constituent such as ammonia or ammonium thereof.

The diagnostic apparatus of the invention can be constructed as a single device with two reaction chambers, one for chemical analysis and one for serological test or immunoassay. The two reaction chambers can also be in physically separate devices used to process for chemical analysis and for serological test portions of a single specimen of body fluid.

A chemical sensor strip can be incorporated as an integrated part of the device or used separately for chemical analysis. The sensor strip comprises at least one porous solid layer impregnated with the necessary reagents for analysis including chemical reaction, separation, and detection.

In the method of the present invention, a sample of the body fluid to be examined is applied to each of the reaction chambers. Ammonia in the fluid is detected in one chamber with a chemical sensor strip or other analytical methods such as ion selective electrode, IC, and HPLC etc. In another chamber, immunochemical information is obtained from the other chamber with immobilized antigen. The immunoassay is based on the formation of antigen-antibody complexes to detect the presence of antibodies or antigens, using antigen to detect antibodies and antibody to detect antigens as required. Generally, antigens of the infectious agent such as *H. pylori* are coated on a solid support. Antibodies present in the sample being examined and specific to the antigen are captured on the solid support, resulting in the formation of antigen-antibody complex. A second antibody labeled with radioactive, enzyme, fluorescent, chemiluminescent or other compound with detectable chemical or physical properties is used to detect the presence of antigen-antibody complex through the formation of an antigen-antibody-anti-antibody complex. Thus, if antibody is present in the sample of a fluid such as saliva, antigen-antibody complexes are formed after a period of incubation when the fluid sample is applied to the chamber. After washing the unbound fluid from the membrane with buffer solution to eliminate non-specific binding, protein-A gold conjugate is added to detect the presence of *H. pylori* antibodies. The Protein-A Gold conjugate binds to the Fc portion of *H. pylori* antibodies captured by antigens on the support. A positive reaction for *H. pylori* antibodies is confirmed by a visible red or slightly pink spot in the test area.

It should be noted that the sketches are not drawn to scale. All the drawings are for illustration of the present invention without limitation.

DESCRIPTION OF THE PREFERRED EMBODIMENTS

Throughout the present specification and claims, "ammonia constituent" is used to refer to any one or more of the species ammonia gas, ammonium ion, and ammonium hydroxide. It has been found that elevated levels of ammonia constituent can be detected in body fluids of persons with active *H. pylori* infection, so that detection and estimation of such levels of ammonia constituent, in combination with serological test for antibody to *H. pylori*, can serve as a diagnostic method for active *H. pylori* infection.

Figure 2A:
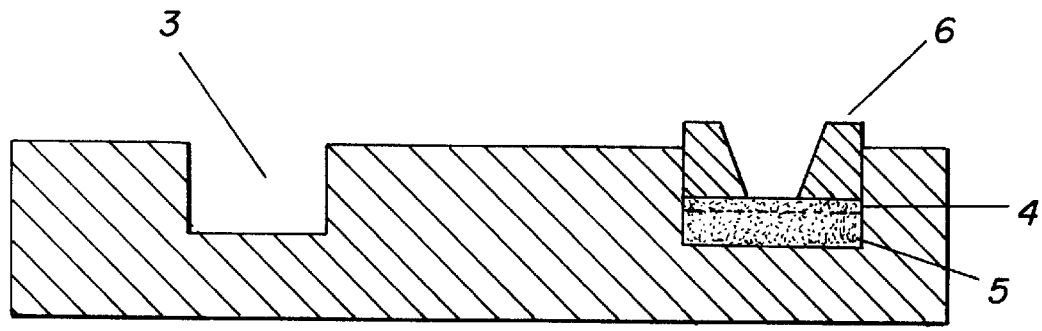
FIG. 2A is a cross-sectional view of the device of FIG. 1 without reagents in the chamber for chemical analysis, 3, and the chamber for immunoassay fitted with reaction membrane 4, absorbance material 5, and cylindrical sample reservoir 6.
Figure 2B:
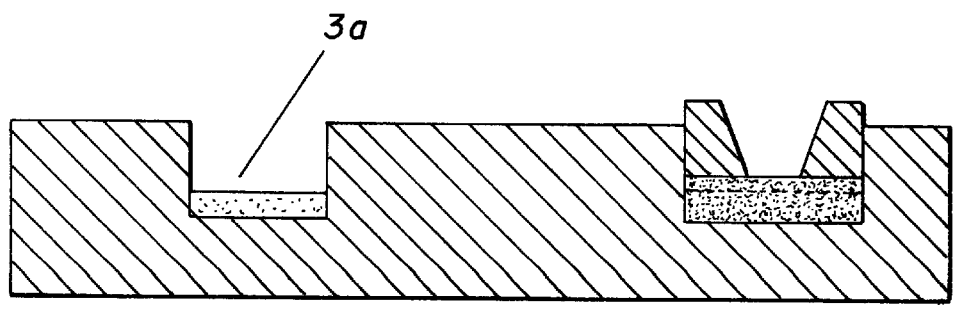
FIG. 2B is a cross-sectional view of the device with immobilized reagents 3$a$ at the bottom of the cell for chemical analysis.

The diagnostic apparatus according to this invention is suitably characterized as having at least one chamber comprising a hollow container with one open end, as illustrated in FIGS. 2A and 2B.

When the container with an open end is the immunoassay chamber, it is suitably characterized as comprising a reaction membrane with immobilized antigen or antibody to said infectious agent, an absorbance layer, and a sample reservoir. The reaction membrane, illustrated at 4 in FIG. 2A, can be any material, organic or inorganic, with sufficient porosity to allow access by samples to be analyzed and with suitable surface affinity to bind antigens. Useful membrane materials include nylon, glass fiber, and natural or synthetic polymers including cellulose esters. The porosity of the membrane can vary from 0.2 to 12 microns. A nitrocellulose (i.e. cellulose nitrate) membrane has excellent absorption and adsorption qualities, and is preferred. Mechanical strength of nitrocellulose membrane is greatly improved with a paper or polyester support. Commercially available paper backed nitrocellulose membrane is conveniently used for easy handling. For the relatively high viscosity of saliva a relatively large porosity grade of membrane is a preferred choice. A binding reagent specific to *H. pylori* antibody, such as a commercially available preparation of *H. pylori* antigen, is immobilized on the membrane and reacts with and captures *H. pylori* antibody when present in the sample of fluid. The thickness of the membrane should be sufficient to immobilize a sufficient amount of antigen to provide adequate sensitivity, but not too thick to block the passage of saliva samples.

The absorbance layer, illustrated at 5 in FIG. 2A, serves to draw liquid through the reaction membrane and can be made of any kind of porous hydrophilic absorbent material, suitably filter paper. The sample reservoir, illustrated at 6 in FIG. 2A, is used to apply a sample to the reaction membrane and keep solution running through the center of the reaction membrane containing the immobilized antigen or antibody.

When the container with an open end is the chemical reaction chamber, it is suitably characterized as comprising a hollow reaction chamber as illustrated at 3 in FIG. 2A in which chemical analysis can be carried out in any of several ways. A sample such as saliva can be added to the cell and mixed with all necessary reagents for producing a detectable response to an analyte of interest in 3. Reaction is allowed to proceed for a certain period of time, then the product is analyzed by HPLC, ion chromatography, ion selective electrodes, uv-vis spectrophotometric method, fluorescence, laser-induced fluorescence or other analytical techniques. For example, saliva sample can be mixed with the reagents such as sodium hydroxide, sodium hypochlorite, sodium salicylate and sodium nitroprusside in the reaction chamber. The mixture is incubated at room temperature for 30 minutes. The absorbance of the solution is measured at 655 nm using a UV-VIS spectrophotometer. The concentration of ammonia constituent in saliva can be obtained from calibration curves of ammonia standard solution.

In a particularly preferred embodiment of this invention, the analyte of interest is an ammonia constituent and an ammonia electrode or a test strip affording a detectable response to ammonia can be used for detection and estimation thereof. An ammonia electrode commercially available from Omega Engineering, Inc. or other manufacturers can be used directly to measure ammonia concentration in saliva. Test strip impregnated with a reagent placed on the top of cell 3 can, for example, also detect ammonia gas generated from an ammonia constituent of a saliva sample placed in the chamber.

As illustrated at 3a in FIG. 2B, reagents necessary for chemical analysis can also be pre-mixed and added to the bottom of the cell. 3a can represent a pure single reagent, a mixture of several reagents, or a reagent impregnated strip prepared by drying porous hydrophilic material such as filter paper soaked with reagent solutions. In the case of reagent impregnated strip, it can be conveniently attached to the bottom of 3 using small amount of epoxy or other adhesive material which does not interfere with the reaction. With reagent or filter paper impregnated with all necessary reagents added to the cell first, one step reaction is carried out by adding saliva or other body fluid sample directly to the cell. 3.

A detectable response to ammonia in accordance with this invention is a change in color of a pH indicator resulting from the reaction of ammonia generated from a sample being examined with the indicator suitably impregnated on a test strip. Suitable pH indicators are characterized by a visible color change at a pH in the range from 4 to 12 and include the following which are preferred.

| Indicator | pH range | Color Change |
| --- | --- | --- |
| 2-(2,4-Dinitrophenylazo)-1-naphthol-3,6-disulfonic acid | 6.0–7.0 | yellow–blue |
| 4,4'-bis(4-amino-1-naphthylazo)-2,2'-stilbenedisulfonic acid | 8.0–9.0 | blue–red |
| 6,8-dinitro-2,4-(1H)quinazolinedione | 6.4–8.0 | colorless–yellow |
| alizarin | 5.6–7.2 | yellow–red |
| brilliant yellow | 6.6–7.8 | yellow–red |
| bromothymol blue | 6.0–7.6 | yellow–blue |
| cresol red | 7.0–8.8 | yellow–red |
| m-nitrophenol | 6.8–8.6 | colorless–yellow |
| metacresol purple | 7.4–9.0 | yellow–purple |
| neutral red | 6.8–8.0 | red–amber |
| phenol red | 6.6–8.0 | yellow–red |
| phenolphthalein | 8.2–10.0 | colorless–pink |
| rosolic acid | 5.0–6.8 | yellow–red |
| thymol blue | 8.0–9.6 | red–blue |
| turmeric | 7.4–8.6 | yellow–red |
| xylenol blue | 8.0–9.8 | yellow–violet |

Another detectable response to ammonia in accordance with this invention is the formation of highly conjugated indophenol dye absorbing strongly at 630–720 nm by reaction of ammonia and a phenol under oxidizing conditions in the so-called Berthelot reaction (see for example P L Searle, Analyst 1984, vol. 109, pages 549–568). An ammonia test strip based on the Berthelot reaction according to this invention is constructed, for example, by soaking porous hydrophilic material such as filter paper with a strong alkali such as sodium hydroxide, an alkali metal salicylate such as lithium salicylate, potassium salicylate, or sodium salicylate, and sodium nitroprusside catalyst, and drying the soaked material so as to avoid overheating, as in an incubator.

A further detectable response to ammonia in accordance with this invention is the formation of a strongly fluorescent product from ammonia and a fluorescence generator reagent such as 4-fluoro-7-nitrobenzo-2-oxa-1,3-diazole (see for example R. Kobayashi et al., Chem. Pharm. Bull. 1992, vol. 40, pages 1327–28).

Figure 3A:
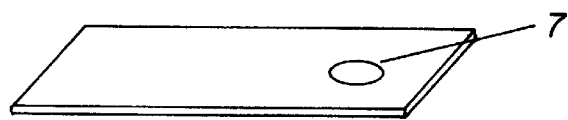
FIG. 3A is a perspective view of an ammonia test strip with multi-layer structure to perform reaction, separation, and detection in one step.
Figure 3B:
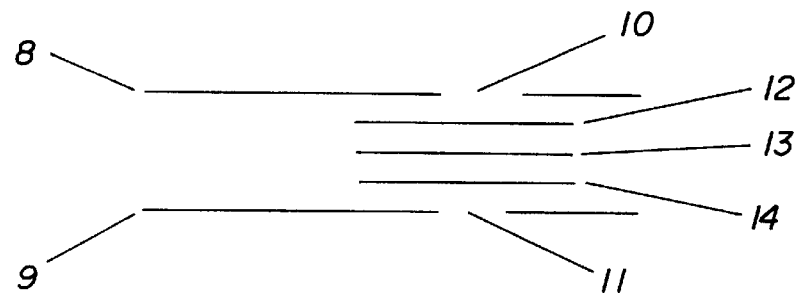
FIG. 3B is a cross-sectional view of an ammonia test strip of FIG. 3A.

Referring to FIG. 3A and FIG. 3B, a one step detection of ammonia constituent in saliva is achieved by using a multi-layer ammonia test strip according to this invention. Such a test strip can consist of reagent layer 12, gas-permeable layer 13, and sensor layer 14 prepared from porous material. 8 and 9 are supporting layers serving to keep 12, 13, and 14 in position. Paper, such as photocopy paper, is a preferred low cost supporting layer, however, synthetic polymers such as polyvinyl chloride can also be used as supporting layer. Paper glue can be used to stick 8 and 9 together. Reagent layer 12 is impregnated with the necessary reagent for chemical reaction, which for ammonia constituent analysis is a strongly basic compound such as sodium hydroxide or potassium hydroxide.

Gas-permeable layer 13 serves to separate volatile analyte such as ammonia from non-volatile interfering substances such as basic inorganic hydroxides, keeping the latter from reaching sensor layer 14. For the fabrication of gas-permeable layer 13, a gas-permeable membrane such as polytetrafluoroethylene, polypropylene, or polyethylene can be used. A particularly preferred gas-permeable layer can be conveniently prepared using cellulose acetate butyrate coated filter paper.

Sensor strip 14 is prepared with pH indicator as illustrated above or with reagents for Berthelot reaction or with fluorescence generator.

When a sample such as saliva is applied to the reagent layer through the hole 10, ammonia constituent in the sample reacts with strong base such as sodium hydroxide in reagent layer and releases ammonia gas. Ammonia gas diffuses through gas-permeable layer 13 and a distinct color change or fluorescence is observed through hole 11 when ammonia reaches sensor layer 14.

Figure 4A:
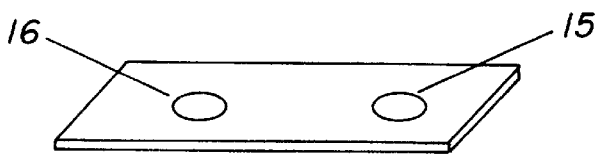
FIG. 4A is a perspective view of an ammonia test strip capable of performing two individual tests at the same time.
Figure 4B:
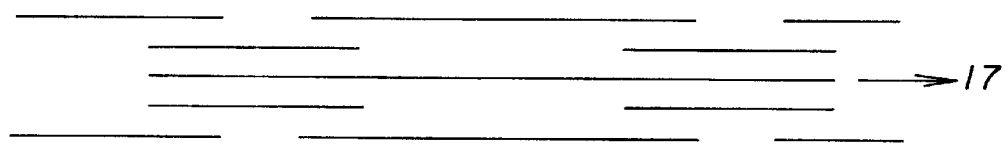
FIG. 4B is a cross-sectional view of an ammonia test strip of FIG. 4A.

In a particularly preferred embodiment, there can be on the ammonia test strip a plurality of sensing units each having an assembly of layers 12, 13, and 14 as shown in FIG. 3B. In this way, two or more samples can be analyzed at the same time using a single test strip as shown in FIG. 4A and FIG. 4B.

Semi-quantitative information can be obtained by running standard and sample simultaneously. To avoid interference, there should be enough space, suitably 8 millimeters, between two sample wells 15 and 16. A single large piece of hydrophobic gas-permeable layer 17 (FIG. 4B) can be used to avoid diffusion of solution from one cell to another.

Figure 5B:
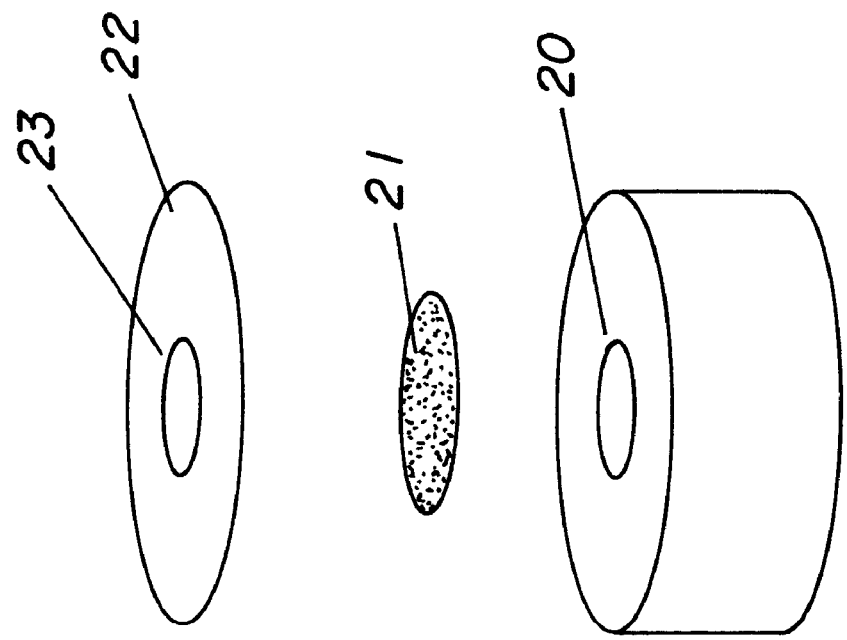
FIG. 5B is an exploded perspective view of top portion of an ammonia test device of FIG. 5A.
Figure 5A:
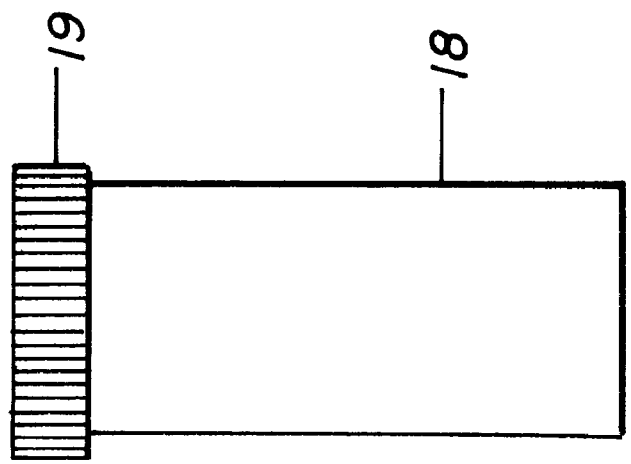
FIG. 5A is a perspective view of an ammonia test device including reaction cell 18 and sensor cap 19.

Referring to FIG. 5A and FIG. 5B, a saliva analyzer for a volatile organic or inorganic analyte such as an ammonia constituent in accordance with this invention includes a reaction cell 18 and a detection cap 19. The reaction cell 18 can be made of any material resistant to chemical attack during the chemical analysis, suitably of glass or plastic. The reaction cell 18 has an open end. The cap 19 can be threaded or clipped onto the cell 18. There is a hole 20 in cap 19, suitably in the middle thereof. A chemical sensor strip 21 can be fixed onto the cap through a solid backing layer 22 with a hole aligned with 20.

Backing layer 22 when used is made of plastic or paper with adhesive material on one side. Instead of using backing layer 22, the sensor strip can be glued directly to the base of the cap using epoxy or other adhesive material.

The sensor strip 21 responds to volatile product, such as ammonia, from the reaction inside the cell 18, resulting in color change, physical property change such as resistance, or the formation of a product which can be determined by various analytical methods such as GC or HPLC. When a sensor strip is impregnated with a pH indicator such as phenol red or cresol red, a distinct color change can be observed through the hole 23 in the backing layer 22. The sensor strip can also be prepared right before the test by applying indicator solution to the strip through top opening 23.

Further disclosure of the invention is provided by the following examples, offered for purpose of illustration and not of limitation.

EXAMPLE 1

Simultaneous Chemical and Immunochemical Analysis

Figure 1:
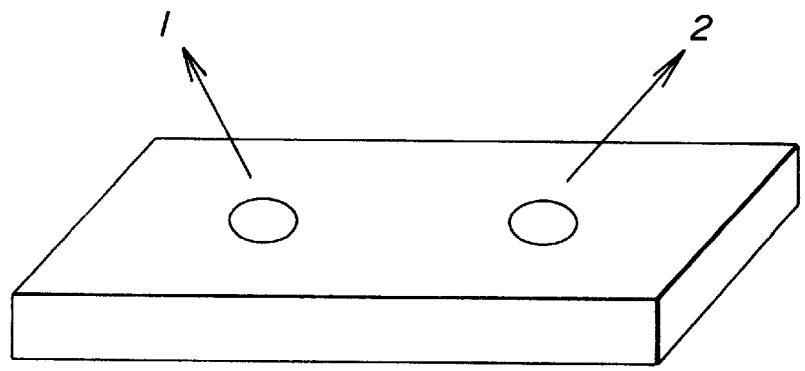
FIG. 1 is a perspective view of a double-chamber reaction device for carrying out chemical and immunochemical analysis simultaneously according to the invention, in which the chambers are identified by the numbers 1 and 2.

In this instance, a device of the type of FIG. 1 was used to carry out chemical and immunochemical analysis.

100 microliters of 10 mM ammonium chloride was added to the cell 1. Then, one drop of 2 M sodium hydroxide was added to the cell. When a test strip impregnated with phenol red indicator was placed on top of the opening, instant color change was observed, indicating the release of ammonia from the reaction.

As an example of immunoassay, H. pylori antigen was immobilized on the reaction membrane 4 in FIG. 2A. Serum or saliva sample containing antibodies to H. pylori was tested using the chamber 2 in FIG. 1. After the sample was absorbed totally through the reaction membrane 4 by absorbance layer 5 in FIG. 2A, washing reagent phosphate buffer containing Tween® 20 surfactant and heat treated normal goat serum was applied. When the washing solution was absorbed, protein A-gold conjugate solution was applied. The treated reaction membrane was incubated at room temperature for 10 minutes and washed again with the washing reagent. A red dot in the middle of the reaction membrane indicated the presence of H. pylori antibodies in the sample.

EXAMPLE 2

Ammonia Test Strips

In this example, preparation of ammonia test strips based on the Berthelot reaction is described. 4.08 g sodium hydroxide (Sigma Chemical Company), 1.19 g sodium salicylate (Aldrich), and 0.05 g sodium nitroprusside (Sigma) were ground into small particles in a porcelain mortar using a porcelain pestle. 5 ml water was added and grinding continued until a fine solid suspension was obtained. The mixture was spread over a piece of Whatman #4 qualitative filter paper and the paper soaked with the reagent was dried overnight in a 40° C. incubator. The filter paper treated in this way was used as an ammonia test strip.

The performance of the test strip was tested using 10 mM ammonium chloride solution. 100 microliters 10 mM ammonium chloride solution was mixed with 100 microliters 5% sodium hypochlorite solution (Sigma). The mixture was applied to the test strip. The color of the strip changed from yellow to green within five minutes.

EXAMPLE 3

Ammonia Test Strips with Gas-permeable Layer

Ammonia test strip shown in FIG. 3A was fabricated. Sensor layer was prepared from 0.02% phenol red or cresol red (Sigma) by soaking and drying a Whatman #4 qualitative filter paper. Gas-permeable layer was prepared by coating a piece of Whatman #4 filter paper with cellulose acetate butyrate. Reagent layer was prepared from 2 M sodium hydroxide solution. All strips were cut into 1 cm×1 cm square pieces. As shown in FIG. 3B, a reagent layer piece, a gas-permeable layer piece, and a sensor layer piece were stacked glued together using two pieces of paper with one hole at one side of the end.

The performance of the test strip was tested using 2 M sodium hydroxide and 10 mM ammonium chloride solution. When one drop of sodium hydroxide solution was applied to hole 10 in FIG. 3B, no color change was observed through hole 11 in FIG. 3B, indicating no leakage of solution through the gas-permeable layer. When ammonium solution was applied, almost instant color change was observed resulting from pH change in the sensor strip due to dissolved ammonia. Saliva sample was also analyzed with the test strip. The test strip was sensitive enough to detect ammonia constituent in the saliva. Ammonia concentration in the saliva was in the millimolar range.

Ammonia test strip as shown in FIG. 4A was prepared using similar procedure. 2.0 mM, 4.0 mM, 6.0 mM, and 8.0 mM ammonium chloride solutions were used to evaluate the performance of the test strip. Two samples were analyzed simultaneously. There was distinct difference in color intensity and color development time when concentration changed with 2.0 mM increment, indicating the possibility to use such a kind of test strip to get semi-quantitative information.

In order to increase color contrast and increase ammonia collection efficiency, test strips are wetted using small volume of distilled water right before analysis.

We claim:

1. A diagnostic apparatus for estimating an active *Helicobacter pylori* infectious agent in human saliva, comprising in combination an immunoassay chamber comprising a reaction membrane with immobilized antigen to said *Helicobacter pylori*, an absorbance layer, and a sample reservoir; a chemical reaction chamber in which said saliva is subjected to chemical analysis for an ammonia constituent thereof selected from the group consisting of ammonia, ammonium ion, and ammonium hydroxide, said chemical reaction chamber comprising a solid porous support impregnated with at least one chemical reagent indicating the presence of said ammonia constituent by a detectable change in electrical potential, in color, or in fluorescence, and said analysis comprising performing a reaction to release ammonia, whereby active *Helicobacter pylori* infection is diagnosed by a positive reaction of said antigen with antibody in said saliva and greater than normal level of ammonia constituent in said saliva.

2. A diagnostic apparatus according to claim 1, in which at least one chamber comprises a hollow container with one open end.

3. A diagnostic apparatus according to claim 1, in which the reaction membrane comprises nitrocellulose.

4. A diagnostic apparatus according to claim 1, in which the absorbance layer comprises porous hydrophilic material.

5. A diagnostic apparatus according to claim 1, in which said chemical reagent is a pH indicator capable of giving rise to a visible change in color at a pH in the range from 4 to 12.

6. A diagnostic apparatus according to claim 7, in which said pH indicator is selected from the group consisting of 2-(2,4-Dinitrophenylazo)-1-naphthol-3,6-disulfonic acid, 4,4'-bis(4-amino-1-naphthylazo)-2,2'-stilbenedisulfonic acid, 6,8-dinitro-2,4-(1H)qunizaolinedione, alizarin, brilliant yellow, bromothymol blue, cresol red, m-nitrophenol, metacresol purple, neutral red, phenol red, phenolphthalein, rosolic acid, thymol blue, turmeric, and xylenol blue.

7. A diagnostic apparatus according to claim 1, in which said chemical reagent responds to the presence of an ammonia constituent by the Berthelot reaction.

8. A diagnostic apparatus according to claim 7, in which said chemical reagent comprises alkali metal hydroxide, alkali metal salicylate, and alkali metal nitroprusside.

9. A diagnostic apparatus according to claim 1, in which said chemical reagent responds to the presence of an ammonia constituent by giving rise to a fluorescent product.

10. A diagnostic apparatus according to claim 9, in which said chemical reagent comprises 4-fluoro-7-nitrobenzo-2-oxa-1,3-diazole.

11. A diagnostic apparatus according to claim 1, in which said porous support comprises an organic polymer.

12. A diagnostic apparatus according to claim 11, in which said porous support comprises cellulose.

13. A diagnostic apparatus according to claim 12, in which said porous support comprises filter paper or cellulose membrane.

14. A diagnostic apparatus according to claim 1, in which the chemical reaction chamber is used to mix saliva with at least one reagent selected from the group consisting of sodium hydroxide, sodium hypochlorite, sodium nitroprusside, and sodium salicylate.

15. A diagnostic apparatus according to claim 1, in which the chemical reaction chamber is used to mix saliva with a reagent for the formation of fluorescent compounds.

16. A diagnostic apparatus according to claim 1, in which the chemical reaction chamber is used to carry out ammonia analysis in saliva using ammonia electrodes.

17. A diagnostic apparatus according to claim 15, in which the reagent for the formation of fluorescent compounds is 4-fluoro-7-nitrobenzo-2-oxo-1,3-diazole.

* * * * *